US012599643B2

(12) United States Patent
Actis Goretta et al.

(10) Patent No.: US 12,599,643 B2
(45) Date of Patent: Apr. 14, 2026

(54) USE OF GREEN COFFEE BASED COMPOSITIONS FOR IMPROVING INSULIN PROFILE

(71) Applicant: SOCIETE DES PRODUITS NESTLE S.A., Vevey (CH)

(72) Inventors: Lucas Actis Goretta, Singapore (SG);
Jacklyn Ruilin Chen, Singapore (SG);
Rachid Bel-Rhlid, Savigny (CH);
Robin Willows, Echandens (CH);
Marine Kraus, Vuarrens (CH);
Christian Chabert, Onex (CH)

(73) Assignee: Societe des Produits Nestle S.A.,
Vevey (CH)

( * ) Notice: Subject to any disclaimer, the term of this
patent is extended or adjusted under 35
U.S.C. 154(b) by 761 days.

(21) Appl. No.: 17/442,213

(22) PCT Filed: Mar. 27, 2020

(86) PCT No.: PCT/EP2020/058696
§ 371 (c)(1),
(2) Date: Sep. 23, 2021

(87) PCT Pub. No.: WO2020/193752
PCT Pub. Date: Oct. 1, 2020

(65) Prior Publication Data
US 2022/0175864 A1 Jun. 9, 2022

(30) Foreign Application Priority Data
Mar. 27, 2019 (EP) ..................................... 19165522

(51) Int. Cl.
A61K 36/74 (2006.01)
A23F 3/16 (2006.01)
(Continued)

(52) U.S. Cl.
CPC ............ *A61K 36/742* (2024.05); *A23F 3/166*
(2013.01); *A23F 3/18* (2013.01); *A23F 3/22*
(2013.01); *A61K 31/192* (2013.01); *A61P 3/10*
(2018.01)

(58) Field of Classification Search
CPC ....... A61K 36/74; A61K 31/192; A23F 3/166;
A23F 3/18; A23F 3/22; A61P 3/10
See application file for complete search history.

(56) References Cited

U.S. PATENT DOCUMENTS

2010/0112098 A1 5/2010 Lemaire et al.

FOREIGN PATENT DOCUMENTS

CN 102014649 A 4/2011
JP 2005333927 A 12/2005
(Continued)

OTHER PUBLICATIONS

Lane et al., Pilot Study of Caffeine Abstinence for Control of
Chronic Glucose in Type 2 Diabetes, 2012, Journal of Caffeine
Research, vol. 2, No. 1, pp. 45-47 (Year: 2012).*
(Continued)

*Primary Examiner* — Trevor Love
(74) *Attorney, Agent, or Firm* — K&L Gates LLP

(57) ABSTRACT
The present invention relates to a green coffee-based com-
position comprising hydrolysed chlorogenic acid for use in
the treatment or prevention of a disorder linked to an
increase in plasma postprandial insulin in a subject. The
invention relates also to the non-therapeutic use of a com-
position comprising an esterase treated decaffeinated green
coffee extract with an amount of 40-200 mg administered to
a subject per day to decrease plasma postprandial insulin
concentration. A further aspect of the invention is a process
for forming green coffee based compositions.

16 Claims, 7 Drawing Sheets

Specification includes a Sequence Listing.

(51) Int. Cl.
| | |
|---|---|
| *A23F 3/18* | (2006.01) |
| *A23F 3/22* | (2006.01) |
| *A61K 31/192* | (2006.01) |
| *A61P 3/10* | (2006.01) |

(56) References Cited

FOREIGN PATENT DOCUMENTS

| | | |
|---|---|---|
| JP | 2018035073 A | 3/2018 |
| WO | 2009132888 | 11/2009 |
| WO | 2012013762 | 2/2012 |

OTHER PUBLICATIONS

Cespedes, Andrea, Recommended Calorie Intake for One Meal, 2017, Livestrong.com, pp. 1-4. (Year: 2017).*

Japanese Office Action for Appl No. 2021-557009 dated Apr. 2, 2024, Document not in English. Considered to the extent of English language translation provided.

Japanese Office Action Received for Application No. 2021-557009, mailed on Apr. 2, 2024, 8 Pages (4 Pages of English Translation and 4 Pages of Official Copy).

Chinese Office Action for Appl No. 202080018054.4 dated Feb. 10, 2025, 7 pages, Considered to the extent that the document is in English.

* cited by examiner

SEQUENCE LISTING

<160> NUMBER OF SEQ ID NOS: 2

<210> SEQ ID NO 1
<211> LENGTH: 747
<212> TYPE: DNA
<213> ORGANISM: Lactobacillus johnsonii

<400> SEQUENCE: 1

```
atggagacta caattaaacg tgatggtcta aacttacatg gtttacttga aggaaccgat      60
aagattgaaa atgatacgat tgctatttta atgcatggtt ttaaaggtga tttgggttat     120
gatgacagca agattttgta tgctctctct cactacttaa atgatcaagg cctcccaaca     180
attcgttttg actttgatgg atgcggaaaa agtgatggta aatttgaaga tatgactgtc     240
tatagcgaaa tcctagatgg gataaaaata ttagattatg ttcgtaatac tgttaaggca     300
aaacatatct atttagtggg acactcccaa ggtggagtag tagcgtcaat gctggctgga     360
tattatcgag atgttattga aaaattggct ttactctctc ctgcagcaac tcttaagtct     420
gatgctttag atggagtttg tcagggtagt acttatgatc caacgcatat ccctgaaact     480
gtcaatgtta gtggctttga gtaggagga gcttacttta gaacggctca attattgcct     540
atttatcaaa cagcggaaca ttataatagg gaaactttat tgattcatgg cttagcagat     600
aaagtcgtgt cacctaatgc ttcaagaaaa tttcatacac ttttgcctaa aagtgagctc     660
catttaattc cagatgaggg tcacatgttt aacggaaaaa atagacctga agtattaaaa     720
ttagttggtg agttttttaat aaaataa                                        747
```

<210> SEQ ID NO 2
<211> LENGTH: 248
<212> TYPE: PRT
<213> ORGANISM: Lactobacillus johnsonii

<400> SEQUENCE: 2

```
Met Glu Thr Thr Ile Lys Arg Asp Gly Leu Asn Leu His Gly Leu Leu
1               5                   10                  15

Glu Gly Thr Asp Lys Ile Glu Asn Asp Thr Ile Ala Ile Leu Met His
            20                  25                  30

Gly Phe Lys Gly Asp Leu Asp Tyr Asp Asp Ser Lys Ile Leu Tyr Ala
        35                  40                  45

Leu Ser His Tyr Leu Asn Asp Gln Gly Leu Pro Thr Ile Arg Phe Asp
    50                  55                  60

Phe Asp Gly Cys Gly Lys Ser Asp Gly Lys Phe Glu Asp Met Thr Val
65                  70                  75                  80

Tyr Ser Glu Ile Leu Asp Gly Ile Lys Ile Leu Asp Tyr Val Arg Asn
                85                  90                  95

Thr Val Lys Ala Lys His Ile Tyr Leu Val Gly His Ser Gln Gly Gly
            100                 105                 110

Val Val Ala Ser Met Leu Ala Gly Tyr Tyr Arg Asp Val Ile Glu Lys
        115                 120                 125

Leu Ala Leu Leu Ser Pro Ala Ala Thr Leu Lys Ser Asp Ala Leu Asp
    130                 135                 140

Gly Val Cys Gln Gly Ser Thr Tyr Asp Pro Thr His Ile Pro Glu Thr
145                 150                 155                 160

Val Asn Val Ser Gly Phe Glu Val Gly Gly Ala Tyr Phe Arg Thr Ala
                165                 170                 175

Gln Leu Leu Pro Ile Tyr Gln Thr Ala Glu His Tyr Asn Arg Glu Thr
            180                 185                 190
```

```
Leu Leu Ile His Gly Leu Ala Asp Lys Val Val Ser Pro Asn Ala Ser
        195             200             205

Arg Lys Phe His Thr Leu Leu Pro Lys Ser Glu Leu His Leu Ile Pro
    210             215             220

Asp Glu Gly His Met Phe Asn Gly Lys Asn Arg Pro Glu Val Leu Lys
225             230             235             240

Leu Val Gly Glu Phe Leu Ile Lys
            245
```

USE OF GREEN COFFEE BASED COMPOSITIONS FOR IMPROVING INSULIN PROFILE

CROSS REFERENCE TO RELATED APPLICATIONS

The present application is a National Stage of International Application No. PCT/EP2020/058696, filed on Mar. 27, 2020, which claims priority to European Patent Application No. 19165522.4, filed on Mar. 27, 2019, the entire contents of which are being incorporated herein by reference.

FIELD OF THE INVENTION

The present invention relates to green coffee-based compositions comprising hydrolysed chlorogenic acid (HDGCE) for use in the treatment or prevention of a disorder linked to an increase in plasma postprandial insulin in a subject, wherein the subject is administered an effective dose of HDGCE with an amount ranging from 40-200 mg/day.

BACKGROUND OF THE INVENTION

Globally it is estimated that there are about 280 million people with type-2 diabetes. The incidence varies substantially in different parts of the world, almost certainly because of genetic, nutritional, environmental and lifestyle factors. In the USA, roughly 21 million patients are diagnosed as having diabetes, 90% of whom are type-2, with a further 8.1 million people estimated to be undiagnosed diabetes sufferers. Diabetes is the $7^{th}$ leading cause of death in the USA. The total cost of diabetes in the United States was $245 billion in 2012. Traditionally considered a disease of adults, type-2 diabetes is increasingly diagnosed in children. This is in parallel with rising obesity rates of children due to alterations in dietary patterns as well as in life style habits.

The primary early development of diabetes may appear when insulin responds to a meal, or more specifically first-phase insulin release, becomes abnormal (Gerich J E, 2002, Diabetes, 51:S117-S121) and elevated blood glucose becomes unavoidable over time. Subsequently, chronic hyperglycemia generates an increased insulin demand and eventually a beta-cell secretory dysfunction causing exhaustion of the beta-cells in the pancreas (Porte D J, 2001, Diabetes Metab Res Rev, 17(3):181-188). This dysfunction of the insulin secretion is believed to appear in parallel to a defect of the hepatic and peripheral insulin action, identified as the insulin resistance which induces elevated fasting blood insulin. Enhanced insulin secretion and insulin resistance both co-operate to increase insulinemia and favour the development of type-2 diabetes. As a consequence, a diminished and adequate response of the insulinemia after a meal could be the sign of an adequate insulin secretion and utilization by the body in healthy or pre-diabetic subjects. This decreased postprandial insulinemia should preserve the pancreatic function and simultaneously improve insulin sensitivity. In the long term, lowering the insulin demand after a meal can reduce (1) the risk of developing type-2 diabetes in pre-diabetic subjects and (2) the deterioration of the glycemic control in type-2 diabetes.

Meng et al., a review article published in Evidence-based complementary and alternative medicine, vol: 2013, article ID 801457 discusses on roles of chlorogenic acid on regulating glucose and lipids metabolism.

WO2009132887 relates to compositions for preparing a coffee beverage comprising hydrolysed chlorogenic acids.

US20150258055 relates to methods for modulating cortisol levels using green coffee bean extract.

US20150209399 relates to methods of enhancement of dehydroepiandrosterone using green coffee bean extract.

There is a persisting need in the food industry to further improve the nutritional solutions provided to diabetic subjects, subjects at risk for developing diabetes and subjects with impaired glucose metabolism.

The object of the present invention is to improve the state of the art and to provide a new and better nutritional solution for improving the postprandial insulin profile in a subject, particularly in a diabetic or pre-diabetic subject.

A further object of the present invention is to improve the state of the art and to provide a new and better nutritional solution for inducing glucose uptake in skeletal muscle cells in a subject, particularly in a diabetic or pre-diabetic subject.

A further object of the present invention is to improve the state of the art and to provide a new and better nutritional solution for improving sensitivity of human pancreatic beta cells to glucose stimulation in a subject, particularly in a diabetic or pre-diabetic subject.

The object of the present invention is achieved by the subject matter of the independent claims. The dependent claims further develop the idea of the present invention.

"Insulin" is a hormone secreted by the beta cells of the pancreas in response to a meal. Insulin is central to regulating carbohydrate and fat metabolism in the body.

A high insulinogenic nutrition represents a chronic stimulus to the beta cells that may induce an adaptive hypertrophy and a progressive dysregulation of the cells, resulting in postprandial hyperinsulinemia. Postprandial hyperinsulinemia may promote weight gain, fat deposition and the development of insulin resistance, metabolic syndrome, glucose intolerance and type-2 diabetes (Kopp W., Metabolism. 2003, July; 52(7):840-844).

SUMMARY OF THE INVENTION

In one aspect, the present invention relates to a green coffee-based composition comprising esterase treated decaffeinated green coffee extract (HDGCE) for use in the treatment or prevention of a disorder linked to an increase in plasma postprandial insulin in a subject wherein the subject is administered an effective dose of esterase treated decaffeinated green coffee extract with an amount of 40-200 mg/day.

In a further aspect, the present invention relates to a green coffee-based composition comprising esterase treated decaffeinated green coffee extract (HDGCE) for use in enhanced skeletal muscle glucose uptake wherein the subject is administered an effective dose of esterase treated decaffeinated green coffee extract with an amount of 40-200 mg/day.

In a further aspect, the present invention relates to a green coffee-based composition comprising esterase treated decaffeinated green coffee extract (HDGCE) for use in improving pancreatic beta cell sensitivity to glucose wherein the subject is administered an effective dose of esterase treated decaffeinated green coffee extract with an amount of 40-200 mg/day.

In one embodiment of the present invention, the subject, in addition to the administration of HDGCE is further complemented with a meal of at least 200 kcal.

It has been surprisingly found by the inventors that consumption of a composition comprising HDGCE decreases the postprandial plasma insulin response in a subject compared to the control group, which consumes a composition without HDGCE. The results of a randomized double-blinded crossover clinical study are disclosed in the examples section. Previous studies have demonstrated using chlorogenic acids which depend on gut in the subject to convert the chlorogenic acids to an active form to mimic HDGCE. It was observed that providing HDGCE after a standardized food challenge has significantly decreased the level of insulin in blood in comparison with no treatment. The significant reduction of insulin (around 20%) is not affecting the glucose levels therefore suggesting that HDGCE is only changing insulin sensitivity.

Blood plasma metabolites detected following dosage with HDGCE in clinical trial subjects were tested on differentiated murine C2C12 skeletal muscle myotubes for effect on glucose uptake in vitro. Treatment of myotubes with individual blood plasma metabolites resulted in enhanced fold change in glucose uptake compared to the control treatment. This data suggests that dosage of DHGCE extract in human patients results in the generation of blood plasma metabolites with the ability to induce enhanced glucose uptake in skeletal muscle cells which could therefore contribute or in part explain the reduced insulin levels observed in the clinical trial.

Accordingly, the present invention provides in a first aspect a composition comprising at least 40 mg of HDGCE (hydrolysed decaffeinated green coffee extract).

In a further aspect, the invention pertains to a non-therapeutic use of a composition comprising at least 40 mg of HDGCE.

In a still further aspect, the present invention pertains to a process for production of HDGCE, comprising the steps of:

Preparing a decaffeinated green coffee extract by contacting green coffee beans with water, steam, organic solvent, super critical $CO_2$ and/or mixtures thereof;

Optionally the decaffeinated green coffee extract is dried (spray or freeze dried);

Contacting the obtained decaffeinated green coffee extract with esterase enzyme (chlorogenate esterase) in a concentration ranging 1 to 20 U/200 mg of green coffee extract W/W dissolved in 1 ml of water or buffer, at pH ranging from 4 to 7 and temperature ranging from 20 to 50° C. for incubation time ranging from 1 to 6 hours;

Heating the above enzyme treated green coffee extract from temperature ranging from 80 to 120° C. for 1 to 30 minutes to deactivate the enzyme and to pasteurize the extract; and Optionally drying the extract to obtain the esterase treated decaffeinated green coffee extract (HDGCE).

4 extract (200 g/L) by L. johnsonii esterase (16.5 U/ml) and formation of caffeic acid (▲) and ferulic acid (♦) as function of time. Reaction volume was 1 ml. The reactions were performed in duplicate.

Figure 6:
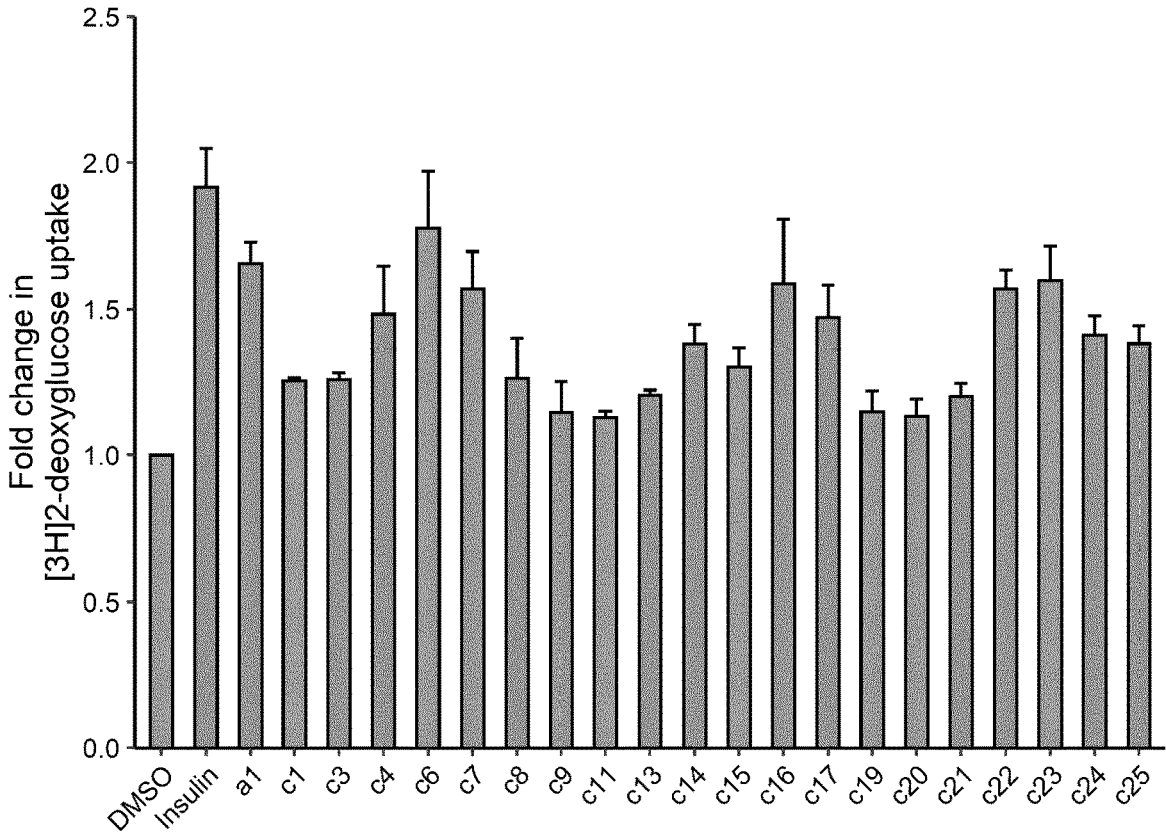

FIG. 6 shows the effect of individual blood plasma metabolites identified following HDGCE dosage on glucose uptake in murine C2C12 skeletal muscle myotubes. Values are shown as fold change relative to control wells and are the average of at least two independent experiments conducted with duplicate or triplicate measurements. Error bars indicate the range or standard error.

Figure 7:
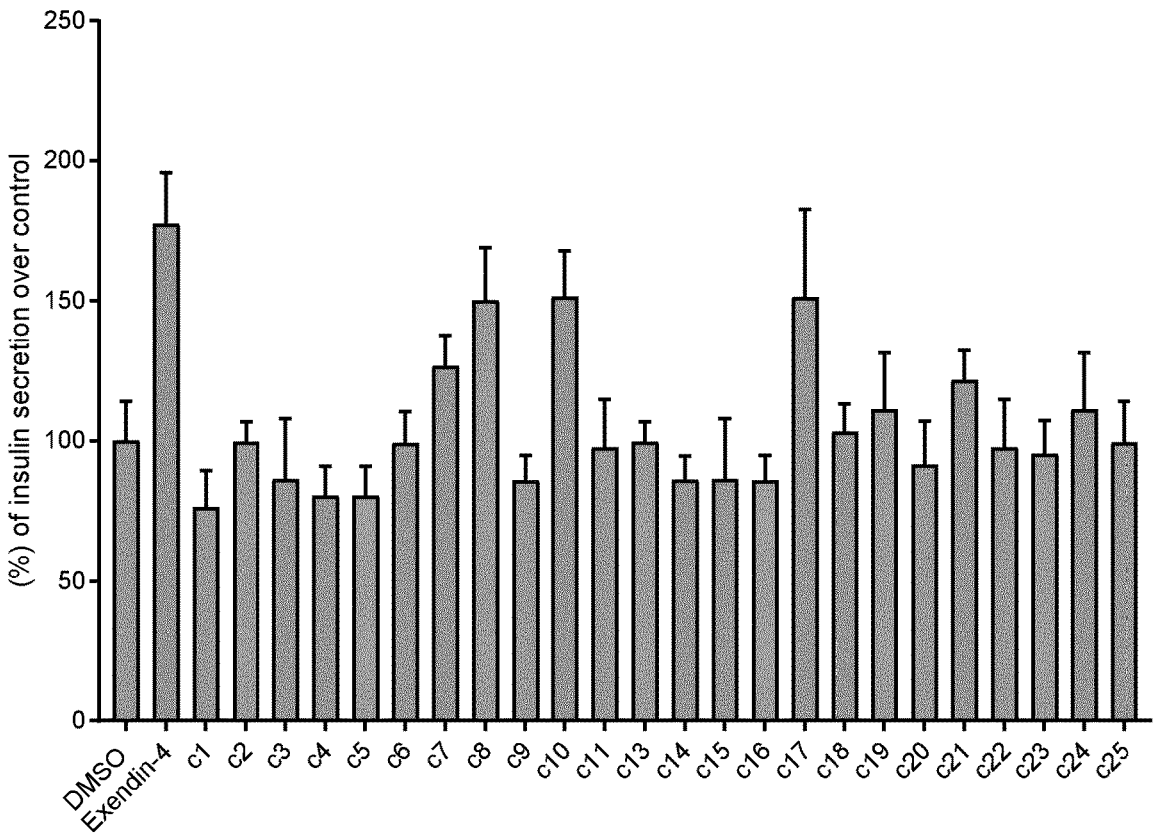

FIG. 7 shows the effect of individual blood plasma metabolites identified following HDGCE dosage on glucose-stimulated insulin secretion in human pseudo-islets. Individual human pseudo-islets were exposed to high glucose solution (16.7 mM) for 2 hours in combination with either DMSO 0.1%, 100 nM Exendin-4 (positive control) or 1 μM metabolite. Effect are expressed as percent effect of the respective insulin secretion in control (DMSO 0.1%), Shown is the average of 6 experiments (mean±SEM).

DETAILED DESCRIPTION OF THE INVENTION

The present invention pertains to a composition comprising a green coffee-based composition comprising esterase treated decaffeinated green coffee extract (HDGCE) for use in the treatment or prevention of a disorder linked to an increase in plasma postprandial insulin in a subject wherein the subject is administered an effective dose of esterase treated decaffeinated green coffee extract with an amount of 40-200 mg/day.

The present invention further pertains to a composition comprising a green coffee-based composition comprising esterase treated decaffeinated green coffee extract (HDGCE) for use in inducing glucose uptake in skeletal muscle cells in a subject wherein the subject is administered an effective dose of esterase treated decaffeinated green coffee extract with an amount of 40-200 mg/day.

The present invention further pertains to a composition comprising a green coffee-based composition comprising esterase treated decaffeinated green coffee extract (HDGCE) for use in improving pancreatic beta cell sensitivity to glucose in a subject, wherein the subject is administered an effective dose of esterase treated decaffeinated green coffee extract with an amount of 40-200 mg/day.

In one embodiment the composition is a liquid beverage composition.

The term "disorder" is selected from the group consisting of diabetes, for example gestational diabetes; impairment of glucose metabolism; hyperinsulinemia or insulin resistance. In one embodiment, the subject is a diabetic or pre-diabetic patient.

In one embodiment of the present invention, the HDGCE composition has a total content of caffeic acid and ferulic acid in a range between 10 and 60 mg. The composition may be a heat-treated composition. In another embodiment of the present invention, the HDGCE composition has ratio of caffeic acid:ferulic acid is at least greater than 2:1. In another embodiment of the present invention, the HDGCE composition has ratio of caffeic acid:ferulic acid ranges from 3:1 to 10:1.

The term "functional food product" means a beverage or food composition comprising at least 40 to 200 mg of HDGCE. The food composition may be a powder form such as chocolate or malt based composition. The food composition may also be a snack such as a cereal bar comprising HDGCE.

The term "esterase treated" refers to incubation of the decaffeinated green coffee extract with purified chlorogenate esterase or microorganism containing such an esterase. A chlorogenate esterase for example is described in U.S. Pat. No. 8,481,028 or for example in Bel-Rhlid et al.: Biotransformation of caffeoyl quinic acids from green coffee extracts by *Lactobacillus johnsonii* NCC 533 (2013): AMB express vol 3:28.

An esterase is a hydrolase enzyme that splits esters into an acid and an alcohol in a chemical reaction with water called hydrolysis. The incubation time can be from 30 minutes to 6 hrs at temperatures ranging from 20 to 50° C. related to concentration of the enzyme such that hydrolysis of at least 80% of total chlorogenic acid present in the decaffeinated green coffee extract is reached. In one embodiment the esterase is from *L. johnsonii*.

The term "decaffeinated green coffee extract" refers to green coffee beans decaffeinated by for instance hot water or extraction with organic solvents or supercritical $CO_2$ well known to a skilled person in the art. The caffeine content is lower than 5%, may be 2 to 3% W/W.

The term "amount of "40-200 mg/day" refers to the esterase treated decaffeinated green coffee extract of 40-200 mg dry weight, which may be dissolved, for instance in water or integrated to a consumable food product such as cereals, soluble coffee, chocolate or food complement such as capsules or tablets fit for consumption by the subject. In one embodiment the amount of esterase treated decaffeinated green coffee extract of 40-200 mg dry weight is dissolved in water.

Typically, postprandial hyper-insulinemia may promote the development of insulin resistance, metabolic syndrome, glucose intolerance and type-2 diabetes [Kopp W., Metabolism. 2003, July; 52(7):840-844]. Lowering the insulin demand after a meal however, can on one hand reduce the deterioration of the glycemic control in type-2 diabetes and on the other hand reduce the risk of developing type-2 diabetes in predisposed subjects. Hence, advantageously, the green coffee based composition as described above are for use in the treatment or prevention of diabetes (for example type-2 diabetes or gestational diabetes), impairment of glucose metabolism, hyperinsulinemia or insulin resistance.

In an embodiment of the invention, the green coffee based composition are for use in a diabetic or pre-diabetic patient. A "pre-diabetic patient" is a subject showing insulin resistance or impaired glucose metabolism and is predisposed, for instance family history, lifestyle or genetics, for developing diabetes later in life. Reducing insulin secretion reduces the risk of the pancreas becoming exhausted in the long term, and so is beneficial for management of the pancreas in pre-diabetes or patients with metabolic disorders. The use of a composition comprising of green coffee based component, in particular a composition comprising esterase treated decaffeinated green coffee extract with an amount of 40-200 mg/day would consequently reduce the risk and/or the development of diabetes, impaired glucose metabolism, hyperinsulinemia or insulin resistance in those subjects.

Prevalence of diabetes, insulin resistance or glucose intolerance is mostly observed in adult humans. However, more and more children are affected, or predisposed or at risk of developing such a disorder later in life. Hence, advantageously, prevention and/or treatment of those disorders should start at a young age. Alternatively, and similarly as observed with humans; diabetes, hyperinsulinemia or insulin resistance are more and more widespread among animals, particularly with animals kept as pets. Hence, the invention also pertains to cats and dogs.

The composition for use according to the invention may be in any suitable format, for example the composition may be in the form of a liquid composition, in the form of a beverage, for example a liquid drink, a shake drink, a nutritional composition or a liquid meal replacement.

An important method of controlling food hygiene risks is to heat treat edible compositions, which may harbour food pathogens or spoilage organisms. Well-known examples of such heat treatments are pasteurization, for example heating an edible material to 70° C. for 2 minutes or 75° C. for 26 seconds or 80° C. for 5 seconds, and ultra-high temperature (UHT) treatment, for example heating an edible material to above 135° C. for at least 2 seconds.

The composition for use according to the invention may be administered in a daily dose to provide HDGCE between 40 mg and 200 mg dry weight per subject per day. Those doses should assure a sufficient daily quantity for providing the desired effect to a subject in at least a mid-term period.

The composition for use according to the invention may be provided as before, part or at the end of a regular meal. For example, the composition may be provided as before, part or at the end of a meal to confer its benefits by reducing the insulin postprandial response in combination with that meal. An improved effect can be expected by providing the composition directly at the end of the meal, for example as part of the dessert.

A further aspect of the present invention is the non-therapeutic use of a green coffee based composition comprising esterase treated decaffeinated green coffee extract with an amount of 40-200 mg/day to decrease plasma postprandial insulin concentration, wherein the amount of caffeic acid and ferulic is in the ratio of caffeic:ferulic is at least more than 2:1, for example 3:1, 4:1, 5:1, 6:1, 7:1, 8:1, 9:1 or 10:1.

It is advantageous that a green coffee based composition comprising esterase treated decaffeinated green coffee extract with an amount of 40-200 mg/day can also be administered to subjects, for example healthy subjects, which may be at risk of developing diabetes type-2, insulin resistance or glucose intolerance at some later time. A composition comprising green coffee as disclosed herein, provides a reduced insulin level after consumption.

Another aspect of the invention provides a process for forming HDGCE composition comprising the steps of; (i) Preparing a decaffeinated green coffee extract by contacting green coffee beans with water, steam, organic solvent, super critical $CO_2$ and/or mixtures thereof; (ii) Optionally drying the decaffeinated green coffee extract; (iii) Contacting the obtained decaffeinated green coffee extract with esterase enzyme, at pH ranging from 4 to 7 and temperature ranging from 20 to 50° C. for incubation time ranging from 1 to 6 hours; (iv) Heating the above enzyme treated green coffee extract from temperature ranging from 80 to 120° C. for 1 to 30 minutes to deactivate the enzyme and to pasteurize the extract; and (v) Drying the extract to obtain the esterase treated decaffeinated green coffee extract (HDGCE). In one embodiment, the drying step (ii) is spray or freeze drying. In another embodiment the esterase enzyme is chlorogenate esterase in a concentration ranging from 1 to 20 U/200 mg of green coffee extract W/W dissolved in 1 ml of water or buffer.

Those skilled in the art will understand that they can freely combine all features of the present invention disclosed herein. In particular, features described for the therapeutic use of the composition may be combined with the non-therapeutic use and vice versa. Further, features described for different embodiments of the present invention may be combined. Further advantages and features of the present invention are apparent from the figures and examples.

EXAMPLES

Example 1

Purification, Characterization and Donning of Esterase from *Lactobacillus johnsonii* (NCC 533)

The esterase activity was identified in *Lactobacillus johnsonii* whole cells. The enzyme was purified and characterized. The gene was annotated (LJ-1228, Gene=1158601 1159347 Reversed Product=alpha/beta hydrolase (see sequences below). The gene was then over-expressed in a food-grade *E. coli* and enzyme purified by HPLC (HIC column TSK gel Phenyl-5PW, Linear gradient of 1 to 0 mol $(NH_4)_2SO_4$/L in $NaPO_4$ (50 mM) pH 7.0+1 mM EDTA. Flow 0.8 ml/min).

DNA Sequence/Nucleotides Sequence

Atggagactacaattaaacgtgatggtctaaacttacatggtttacttg aaggaaccgataagattgaaaatgatacgattgctattttaatgcatgg tttaaaggtgatttgggttatgatgacagcaagattttgtatgctctc tctcactacttaaatgatcaaggcctcccaacaattcgttttgactttg atggatgcggaaaaagtgatggtaaatttgaagatatgactgtctatag cgaaatcctagatgggataaaaatattagattatgttcgtaatactgtt aaggcaaaacatatctatttagtgggacactcccaaggtggagtagtag cgtcaatgctggctggatattatcgagatgttattgaaaaattggcttt actctctcctgcagcaactcttaagtctgatgctttagatggagtttgt cagggtagtacttatgatccaacgcatatccctgaaactgtcaatgtta gtggctttgaagtaggaggagatactttagaacggctcaattattgcct atttatcaaacagcggaacattataatagggaaactttattgattcatg gatagcagataaagtcgtgtcacctaatgcttcaagaaaatttcataca cttttgcctaaaagtgagctccatttaattccagatgagggtcacatgt ttaacggaaaaaatagacctgaagtattaaaattagttggtgagttttt aataaaataa Amino Acid Sequence

| | | |
|---|---|---|
| 1 | mettikrdgl nlhgllegtd kiendtiail mhgfkgdldy ddskilyals hylndqglpt |
| 61 | irfdfdgcgk sdgkfedmtv yseildgiki ldyvrntvka khiylvghsq ggvvasmlag |
| 121 | yyrdviekla llspaatlks daldgvcqgs tydpthipet vnvsgfevgg ayfrtaqllp |
| 181 | iyqtaehynr etllihglad kvvspnasrk fhtllpksel hlipdeghmf ngknrpevlk |
| 241 | lvgeflik |

8

Identification of Optimal pH of *L. johnsonii* Esterase

Figure 2:
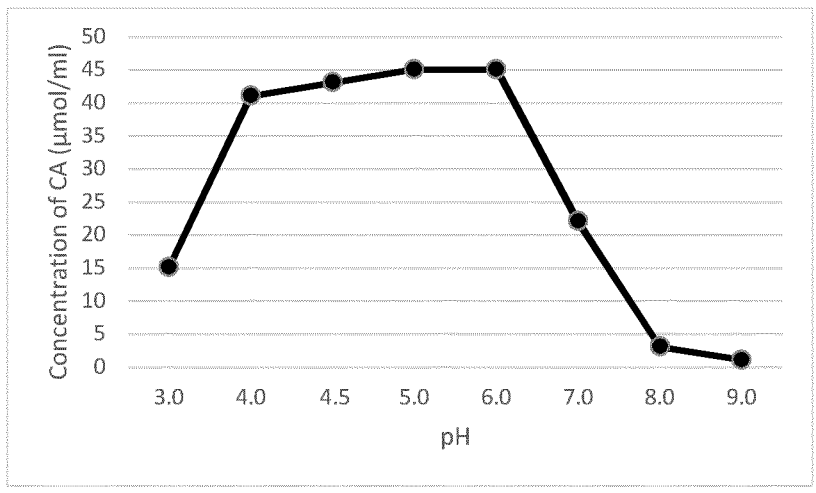
FIG. 2 shows effect of pH on the L. johnsonii esterase activity.

The optimum pH was determined by using glycine buffer, acetate buffer, Tris buffer, phosphate buffer and water. 5-CQA was used as substrate (50 µmol/ml). As we can see in FIG. 2, the optimum pH of the enzyme was between 4.0 and 6.0. The reactions were performed for 30 min at 37° C. with purified esterase (0.01 U/mg substrate)

Identification of Optimal Temperature of *L. johnsonii* Esterase

Figure 3:
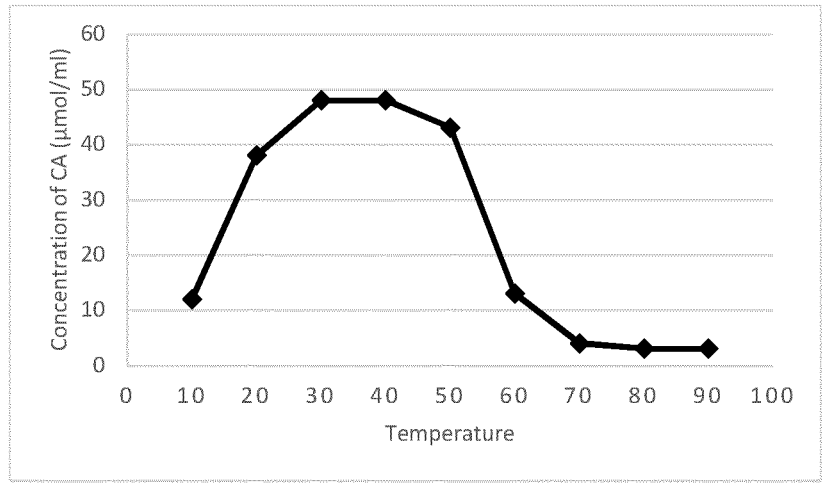
FIG. 3 shows effect of temperature on the L. johnsonii esterase activity.

The optimum temperature was determined by using 5-CQA as substrate (50 µmol/ml) at different temperatures from 10° C. to 90° C. As we can see in FIG. 3, the optimum temperature of the enzyme was between 30° C. and 40° C. The reactions were performed for 30 min at pH 5.0 with purified esterase (0.01 U/mg substrate)

Substrate Specificity

Figure 4:
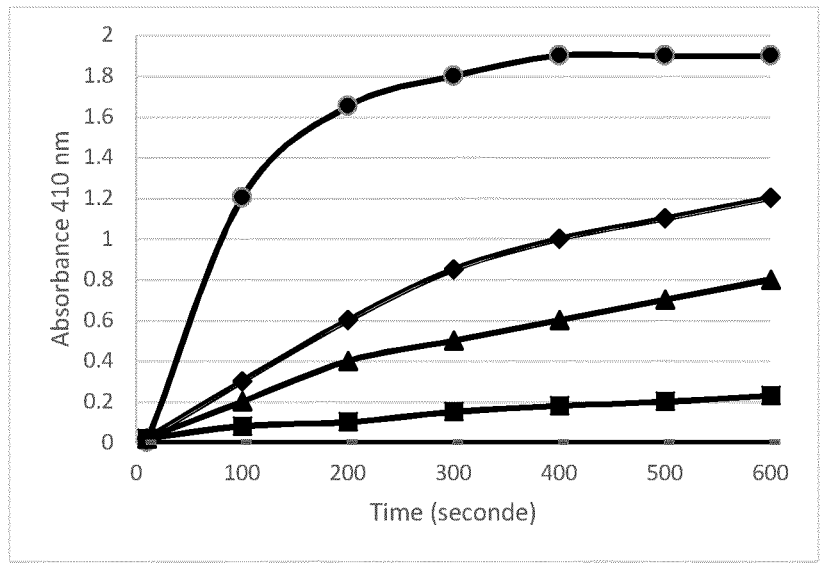
FIG. 4 shows substrate specificity of L. johnsonii esterase. 4-nitrophenyl butyrate (●); 4-nitrophenyl acetate (♦); 4-nitrophenyl decanoate (▲); 4-nitrophenyl tetradecanoate (■); 4-nitrophenyl dodecanoate (▬).

The substrate specificity of *L. johnsonii* esterase was studied using different 4-nitrophenyl derivatives. As we can see in FIG. 4, 4-nitrophenyl butyrate was the best substrate while no transformation of 4-nitrophenyl dodecanoate could be observed. The reactions were carried out in sodium phosphate buffer pH 6.0 at 37° C. for 10 min. The substrates were used at concentration of 0.2 mM and enzyme at 0.01 U/mg substrate. The measures were monitored each 30 seconds. The absorbance was set at 410 nm.

Treatment of Decaffeinated Green Coffee Extract with *L. johnsonii* Esterase.

Reaction Kinetics: Lab Scale Trials

Kinetic studies were performed on decaffeinated green coffee extract (200 mg/ml) using *L. johnsonii* esterase at different concentrations (1.65, 3.3, 4.95, 8.25 and 16.25 U/ml). The reactions were performed in 1 ml volume, at pH 4.5 and 37° C. The results are summarized in the following tables. The concentrations of the different compounds are in mg/ml.

| | Time (h) | | | | |
|---|---|---|---|---|---|
| | 0 | 1 | 2 | 3 | 4 |
| Enzyme (U) | 0 | 1.65 | 1.65 | 1.65 | 1.65 |
| DGCE (mg/ml) | 200 | 200 | 200 | 200 | 200 |
| CQAs | 52.11 | 21.51 | 18.05 | 16.18 | 15.14 |
| FQAs | 11.03 | 9.89 | 9.09 | 9.56 | 8.3 |
| di-CQAs | 13.22 | 3.34 | 2.88 | 2.65 | 2.44 |
| CA | 0.49 | 19.82 | 21.51 | 22.35 | 22.08 |
| FA | 0.21 | 3.76 | 4.11 | 4.45 | 4.36 |
| Caffeine | 3.20 | 3.13 | 3.09 | 3.10 | 3.00 |

| | Time (h) | | | | |
|---|---|---|---|---|---|
| | 0 | 1 | 2 | 3 | 4 |
| Enzyme (U) | 0 | 3.3 | 3.3 | 3.3 | 3.3 |
| DGCE (mg/ml) | 200 | 200 | 200 | 200 | 200 |

-continued

| | Time (h) | | | | |
| --- | --- | --- | --- | --- | --- |
| | 0 | 1 | 2 | 3 | 4 |
| CQAs | 52.25 | 17.77 | 14.62 | 12.88 | 11.09 |
| FQAs | 11.1 | 1.65 | 1.46 | 1.28 | 1.11 |
| di-CQAs | 13.29 | 2.41 | 2.14 | 2.08 | 1.83 |
| CA | 0.48 | 25.63 | 27.23 | 27.56 | 26.27 |
| FA | 0.20 | 4.09 | 4.58 | 4.77 | 4.80 |
| Caffeine | 3.21 | 3.05 | 3.08 | 3.04 | 2.90 |

| | Time (h) | | | | |
| --- | --- | --- | --- | --- | --- |
| | 0 | 1 | 2 | 3 | 4 |
| Enzyme (U) | 0 | 4.95 | 4.95 | 4.95 | 4.95 |
| DGCE (mg/ml) | 200 | 200 | 200 | 200 | 200 |
| CQAs | 50.85 | 15.88 | 12.86 | 10.93 | 10.04 |
| FQAs | 10.74 | 1.66 | 1.29 | 1.07 | 0.57 |
| di-CQAs | 11.75 | 1.83 | 1.72 | 1.44 | 1.37 |
| CA | 0.49 | 26.42 | 27.77 | 27.82 | 27.65 |
| FA | 0.21 | 4.30 | 4.79 | 4.94 | 5.19 |
| Caffeine | 3.12 | 3.03 | 3.04 | 2.94 | 2.98 |

| | Time (h) | | | | |
| --- | --- | --- | --- | --- | --- |
| | 0 | 1 | 2 | 3 | 4 |
| Enzyme (U) | 0 | 8.25 | 8.25 | 8.25 | 8.25 |
| DGCE (mg/ml) | 200 | 200 | 200 | 200 | 200 |
| CQAs | 51.68 | 13.03 | 9.78 | 8.07 | 6.93 |
| FQAs | 10.92 | 1.32 | 0.56 | 0.50 | 0.49 |
| di-CQAs | 13.48 | 1.53 | 1.17 | 0.95 | 0.90 |
| CA | 0.48 | 27.13 | 28.52 | 29.22 | 29.40 |
| FA | 0.21 | 4.90 | 5.72 | 6.08 | 6.36 |
| Caffeine | 3.20 | 2.97 | 2.95 | 2.94 | 2.92 |

| | Time (h) | | | | |
| --- | --- | --- | --- | --- | --- |
| | 0 | 1 | 2 | 3 | 4 |
| Enzyme (U) | 0 | 16.5 | 16.5 | 16.5 | 16.5 |
| DGCE (mg/ml) | 200 | 200 | 200 | 200 | 200 |
| CQAs | 51.46 | 8.90 | 6.34 | 4.87 | 3.91 |
| FQAs | 10.93 | 0.54 | 0.48 | 0.44 | 0.42 |
| di-CQAs | 13.19 | 1,29 | 1.02 | 0.58 | 0.30 |
| CA | 0.48 | 27.26 | 28.79 | 29.19 | 29.90 |
| FA | 0.21 | 4.90 | 5.72 | 6.08 | 6.36 |
| Caffeine | 3.18 | 2.80 | 2.83 | 2.79 | 2.82 |

Reaction Kinetics as Function of Time

Kinetic studies were performed on decaffeinated green coffee extract (200 mg/ml) using *L. johnsonii* esterase at concentration of 16.25 U/ml. The reactions were performed in 1 ml reaction volume, at pH 4.5 and 37° C. The kinetics were carried out for 1, 2, 3 and 4 hours. The concentration of the different compounds are in mg/ml.

Reaction Kinetics as Function of Enzyme Concentration

Figure 5:
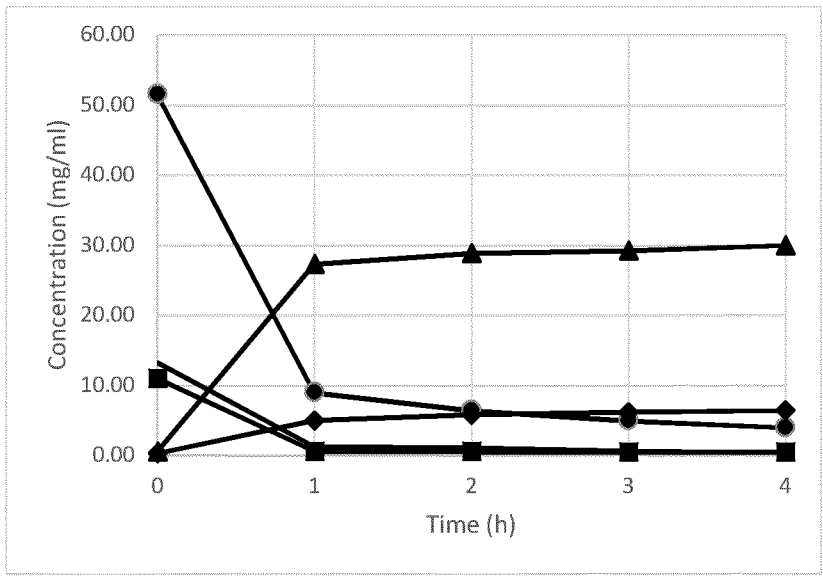
FIG. 5 shows Kinetic transformation of CQAs (♦); FQAs (■); and di-CQAs (▬) from decaffeinated green coffee

Kinetic studies were performed on decaffeinated green coffee extract (200 mg/ml) using *L. johnsonii* esterase at different concentrations (5, 10, 15, 25 and 50 μl/ml that correspond respectively to 1.65, 3.3, 4.95, 8.25 and 16.5 U/ml). The reactions were performed in 1 ml volume, at pH 4.5 and 37° C. (see FIG. 5). The reactions time was 4 hours. The concentration of the different compounds are in mg/ml.

Pilot Plant Trial

Treatment of Decaffeinated Green Coffee Extract with *L. johnsonii* Esterase

Decaffeinated green coffee extract (1.76 Kg) was dissolved in water (8.8 Kg) under stirring. The pH was then adjusted to pH 4.5 by addition of chlorhydric acid (HCl, 0.36 Kg). To this solution, 0.024 Kg of enzyme (Esterase from *L. johnsonii*) was added in two times: 0.016 Kg of enzyme was added at time T=0 h and 0.008 Kg of enzyme was added after 3 h of reaction. The reaction was performed at 37° C. for 6 hours. The mixture was then heated for 10 min at 98° C. to inactive the enzyme. After centrifugation (2 min at 5000 g) and filtration (0.45 μm), the mixture was freeze-dried and the resulting powder was used for the preparation of beverages used for clinical study.

UPLC Analysis

The method used to analyze the samples allows the quantitative determination of caffeic acid, chlorogenic acid isomers (5-CQA, 4-CQA, 3-CQA, 4-FQA, 5-FQA, 3,4-diCQA, 3,5-diCQA and 4,5-diCQA) and caffeine in liquid coffee extract and pure soluble coffee, extracted either from roasted or green beans. The samples were centrifuged (5000 g) for 5 min at 15° C. 100 μL of the resulting supernatant were added to 900 μL of methanol/water (80:20) and filtered on 0.2 μm before analysis. The analyses were performed on an UPLC equipped with a pump, a degassing system, a sample injector with injection loop more than 5 μL, an photodiode array detector (325 and 275 nm wavelength) and an appropriate data software. The separation of molecules was carried on an ACQUITY UPLC BEH Shield RP 18, 1.7 μm, 2.1×100 mm, column (from Waters). Mobile phase A was 5% acetonitrile in water with 0.1% phosphoric acid and mobile phase B was 100% acetonitrile with 0.1% phosphoric acid. Flow rate was 0.4 mL/min, column temperature 35° C. and injection volume was 2 μL.

Clinical Trial

HDGCE was be tested on the Glucose response (GR) and Insulin response (IR) in comparison to a placebo (crossover, randomized, single blind trial). A total of twelve (12) subjects participated in the study. Each subject went into the study site between 7:30 am to 3:00 pm on 2 separate days after 10-14 hour overnight fast.

The following was done on both visits:

Subjects remained seated quietly during the entire test session. Subjects did not smoke, consumed alcohol, coffee (in any form) or involved in any unusual vigorous physical activity for 24 hours prior to test. When volunteers arrived to the site, a cannula was inserted into a vein for blood sampling. 5 ml of whole blood was drawn during fasting state. Then, volunteers received a standardized food challenge. Similar to the Oral Glucose Tolerance test (OGTT), a mixed macronutrient challenge has been recently proposed as optimal nutritional stressor to be used in nutrition research by Stroeve et al (13). The food challenge was be prepared by the research staff from two commercially available products. Briefly, 237.5 ml of a nutritional drink plus 100 ml of whipping cream was stirred and served in a glass/bottle. The subjects were asked to consume the food challenge followed by the treatment within a 15 minutes time frame. Further venous blood samples (3 ml) were drawn at 15 min, 30 min, 45 min, 60 min(1 h), 90 min(1.5 h), 120 min(2 h), 180 min(3 h), 240 min(4 h), 300 min(5 h) and 360 min(6 h) after the food is consumed. A minimum of two days washout period was allowed between the administrations of the treatments.

The collected blood samples at 0 min, 15 min, 30 min, 45 min, 60 min (1 h), 90 min (1.5 h), 120 min (2 h), 180 min (3 h), 240 min (4 h), 300 min (5 h) and 360 min (6 h) were analyzed for blood glucose and insulin. Blood glucose was analyzed using calibrated YSI 2300 Stat Plus Glucose and Lactate analyzer and insulin was determined by Insulin (human) AlphaLISA Detection Kit and read by EnSpire Alpha Plate Reader. The glucose and insulin values were plotted against time to determine the Incremental Area Under Curve (IAUC).

Statistical Considerations

All data were log-transformed to achieve normality of the residuals in the models. Hence, all the treatment effects are expressed as ratios of geometric means. Geometric mean is an estimate of the median. In Table 2, when a model-based treatment effect is below 1, the values estimated (AUC or Cmax) are higher in the placebo group. If the ratio is greater than 1, the estimation is higher in the coffee extract group. AUC and Cmax refer to incremental AUC and incremental Cmax, respectively.

The treatment effect on tmax was estimated using the Wilcoxon signed-rank test, a non-parametric statistical test. The estimates presented in Table 2 for tmax are the Hodges-Lehmann estimates which are estimates of differences of medians between treatment groups.

Insulin

TABLE 3

| Insulin: Summary statistics by treatment and by timepoint | | | | | | | | |
|---|---|---|---|---|---|---|---|---|
| Timepoint | n | mean | sd | geomean | geosd | median | min | max |
| Placebo | | | | | | | | |
| 15 min | 12. | 27.27 | 27.04 | 19.74 | 2.27 | 19.90 | 4.40 | 105.70 |
| 30 min | 12 | 49.44 | 22.52 | 45.68, | 1.49 | 41.35 | 29.20 | 102.30 |
| 45 min | 12 | 56.70 | 32.77 | 48.41 | 1.82 | 49.20 | 21.60 | 117.40 |
| 60 min | 12 | 57.94 | 33.89 | 48.27 | 1.97 | 50.55 | 14.40 | 123.20 |
| 90 min | 12 | 55.94 | 35.11 | 46.25 | 1.94 | 46.05 | 16.10 | 122.80 |
| 120 min | 12 | 60.36 | 36.01 | 49.45 | 2.01 | 52.55 | 12.90 | 112.90 |
| 300 min | 12 | 53.21 | 39.93 | 39.07 | 2.36 | 42.30 | 12.00 | 118.50 |
| 240 min | 12 | 19.26 | 20.74 | 11.37 | 2.91 | 8.45 | 3.50 | 60.70 |
| 300 min | 12 | 6.33 | 4.55 | 4.80 | 2.23 | 3.95 | 1.40 | 13.90 |
| 360 min | 12 | 4.16 | 3.21 | 3.18 | 2.18 | 2.45 | 0.70 | 11.10 |
| Coffee Extract | | | | | | | | |
| 15 min | 12 | 25.44 | 17.91 | 20.04 | 2.12 | 21.00 | 5.40 | 64.80 |
| 30 min | 12 | 48.43 | 37.19 | 38.55 | 1.98 | 34.25 | 14.40 | 133.80 |
| 45 min | 12 | 52.37 | 42.51 | 38.88 | 2.35 | 41.95 | 5.80 | 151.90 |
| 60 min | 12 | 49.27 | 27.83 | 43.80 | 1.62 | 40.05 | 24.10 | 105.30 |
| 90 min | 12 | 42.11 | 16.81 | 39.30 | 1.47 | 38.75 | 23.50 | 74.00 |
| 120 min | 12 | 45.93 | 26.70 | 38.71 | 1.89 | 42.60 | 13.40 | 103.20 |
| 180 min | 12 | 39.57 | 23.44 | 31.74 | 2.14 | 40.15 | 8.10 | 81.30 |

TABLE 1

| Insulin: summary of statistics of AUC, $C_{max}$ and $t_{max}$ by treatment | | | | | | | | |
|---|---|---|---|---|---|---|---|---|
| Insulin | n | mean | sd | geomean | geosd | median | min | max |
| AUC (mU * min/L) | | | | | | | | |
| Placebo | 12 | 10796.19 | 5493.58 | 9354.14 | 1.80 | 10923.66 | 3235.21 | 17994.00 |
| Coffee Extract | 12 | 8758.97 | 3997.48 | 7815.34 | 1.70 | 7779.23 | 2485.87 | 16030.34 |
| Cmax (mU/L) | | | | | | | | |
| Placebo | 12 | 78.04 | 32.36 | 71.15 | 1.60 | 78.09 | 30.40 | 121.10 |
| Coffee Extract | 12 | 63.28 | 34.45 | 55.65 | 1.70 | 57.30 | 21.00 | 143.40 |
| tmax (min) | | | | | | | | |
| Placebo | 12 | 100.00 | 57.33 | 84.49 | 1.87 | 90.00 | 30.00 | 180.00 |
| Coffee Extract | 12 | 96.25 | 61.50 | 75.27 | 2.22 | 90.00 | 15.00 | 180.00 |

TABLE 2

| Model-based estimated treatment effects with 95% CI. For AUC and Cmax, the estimates reported are ratios of geometric means of Coffee Extract over Placebo. For tmax, the estimate of the difference of medians between Coffee Extract and placebo is Reported. | | | | |
|---|---|---|---|---|
| Coffee Extract vs Placebo | Estimate | Lower | Upper | p-value |
| AUC | 0.830 | 0.676 | 1.020 | 0.071 |
| Cmax | 0.772 | 0.631 | 0.946 | 0.018 |
| tmax | −4.813 | −60.000 | 45.000 | 0.888 |

TABLE 3-continued

| Insulin: Summary statistics by treatment and by timepoint | | | | | | | | |
|---|---|---|---|---|---|---|---|---|
| Timepoint | n | mean | sd | geomean | geosd | median | min | max |
| 240 min | 12 | 19.47 | 21.30 | 10.35 | 3.57 | 8.65 | 1.00 | 66.00 |
| 300 min | 12 | 6.19 | 6.00 | 4.40 | 2.32 | 3.90 | 1.20 | 22.50 |
| 360 min | 12 | 4.75 | 5.02 | 3.06 | 2.61 | 2.25 | 0.70 | 16.30 |

TABLE 4

| Glucose: Summary statistics of AUC, Cmax and tmax by treatment | | | | | | | | |
|---|---|---|---|---|---|---|---|---|
| Glucose | n | mean | sd | geomean | geosd | median | min | max |
| AUC (mmol * min/L) | | | | | | | | |
| Placebo | 12 | 225.82 | 174.68 | 171.61 | 2.27 | 197.17 | 33.00 | 671.45 |
| Coffe Extract | 12 | 207.82 | 146.25 | 142.16 | 3.04 | 178.07 | 8.75 | 427.76 |

TABLE 4-continued

| Glucose: Summary statistics of AUC, Cmax and tmax by treatment | | | | | | | | |
|---|---|---|---|---|---|---|---|---|
| Glucose | n | mean | sd | geomean | geosd | median | min | max |
| Cmax (mmol/L) | | | | | | | | |
| Placebo | 12 | 2.08 | 0.98 | 1.87 | 1.65 | 1.96 | 0.65 | 4.37 |
| Coffee Extract | 12 | 1.93 | 0.86 | 1.73 | 1.65 | 1.83 | 0.67 | 3.41 |
| tmax (min) | | | | | | | | |
| Placebo | 12 | 110.00 | 95.80 | 80.53 | 2.28 | 90.00 | 30.00 | 360.00 |
| Coffee Extract | 12 | 67.50 | 58.79 | 50.24 | 2.17 | 45.00 | 15.00 | 180.00 |

Figure 1:
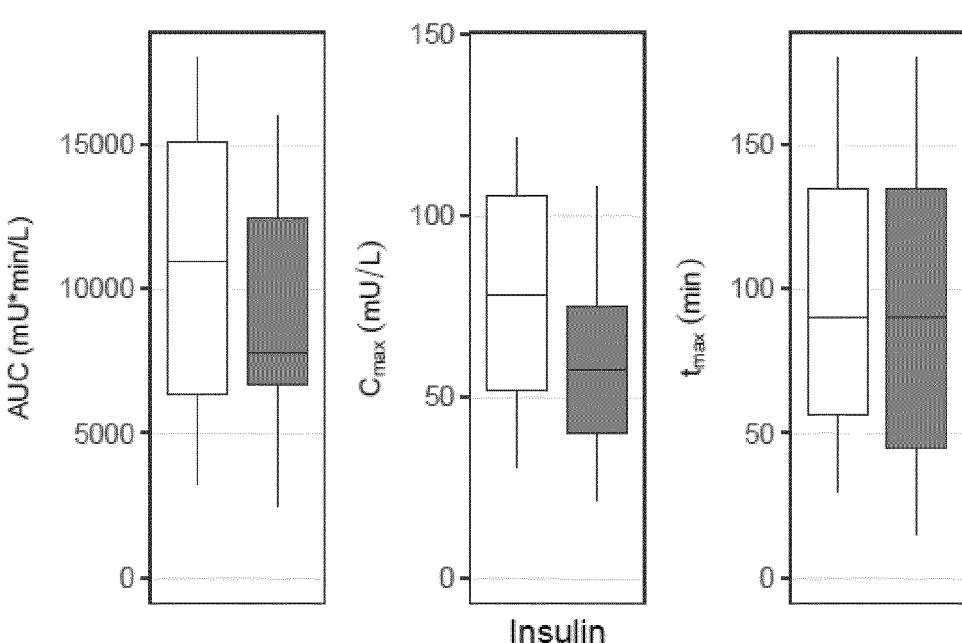
FIG. 1 shows box plots of area under the curve (AUC), maximum concentration (Cmax) and time to maximum concentration (tmax) by treatment.

Our findings showed that a single ingestion of HDGCE significantly decreased insulin concentration in plasma by around 20% in 12 subjects after a nutritional food challenge (p=0.02) (see tables 1, 2 and 3). Glucose concentration in plasma did not shown any difference between a single ingestion of hydrolysed decaffeinated green coffee extract or placebo treatment (table 4). However, in vitro data shows that the metabolites increases the glucose uptake in the skeletal muscle cells. Therefore, we concluded that hydrolysed decaffeinated green coffee extract improve insulin sensitivity in humans. Results also showed an almost statistical significance difference in insulin AUC (mmol*min/L) (p=0.07) with the HDGCE compared to placebo (see FIG. 1, table 2).

In Vitro Test: Glucose Uptake

Murine C2C12 myoblasts were grown in Dulbecco's Modified Eagle Medium (DMEM) 4.5 g/L glucose with GlutaMAX supplemented with 20% fetal bovine serum (vol/vol), 50 μM palmitate, 0.3% bovine serum albumin with 100 U/ml penicillin G and 100 μg/ml streptomycin and maintained at 37° C. with 5% carbon dioxide. Cells were plated and differentiated to form myotubes in DMEM 4.5 g/L glucose with GlutaMAX supplemented with 1% horse serum (vol/vol)), 50 μM palmitate, 0.3% bovine serum albumin with 100 U/ml penicillin G and 100 μg/ml streptomycin. Differentiated myotubes were treated with individual plasma metabolites at 10 μM and 0.1% (vol/vol) dimethyl sulphoxide in serum free DMEM 4.5 g/L glucose with GlutaMAX, 50 μM palmitate, 0.3% bovine serum albumin for 18 hours at 37° C. with 5% carbon dioxide. Cells were transferred to krebs-ringers-hepes buffer (140 mM sodium chloride, 4.7 mM potassium chloride, 2.5 mM calcium chloride, 1.25 mM magnesium sulphate, 1.2 mM potassium dihydrogen phosphate, 10 mM 4-(2-Hydroxyethyl)piperazine-1-ethanesulfonic acid pH 7.4) with 2 mM sodium pyruvate, 50 μM palmitate, 0.3% bovine serum albumin and compounds at 10 μM and 0.1% (vol/vol) dimethyl sulphoxide for four hours at 37° C. with 5% carbon dioxide. 50 μM 2-deoxyglucose containing [3H]2-deoxyglucose was then added to the cells for 5 minutes at 37° C. with 5% carbon dioxide. The reaction was stopped with addition of 25 mM glucose. The myotubes were washed extensively with phosphate buffered saline, lysed in 0.1 M sodium hydroxide and the amount of radiolabel incorporated was detected by liquid scintillation counting. Changes in the amount of [3H]2-deoxyglucose incorporated was determined relative to control wells and presented as fold change. Positive control treatment with a well known AMPK activator (denoted herein as "al") was performed at 5 μM for the full treatment period and insulin was added for 4 hours in KRH buffer at 10 nM.

In Vitro Test: Insulin Secretion

3D InSight™ Human Islet Microtissues were obtained from InSphero AG (Switzerland). Upon arrival the pseudo-islets were treated following manufacturer's instruction for measurement of glucose stimulated insulin secretion. Briefly, the isolated pseudo-islets were carefully washed twice and incubated for 1 h at low glucose in modified Krebs-Ringer buffer (KRB) containing (in mM): 131 NaCl, 4.8 KCl, 1.3 $CaCl_2$, 1.2 $KH_2PO_4$, 1.2 $MgSO_4$, 5 $NaHCO_3$, 25 HEPES, 2.8 glucose and 0.5% BSA. This solution is referred to as LGS (low glucose solution, 2.8 mM). Then isolated islets were carefully washed with LGS and incubated for 2 h in fresh KRB containing 16.7 mM glucose, 0.5% BSA in presence of test substances at 1 μm final concentrations. Measures of insulin levels in supernatants and cell extracts (extraction in acid ethanol (1.5% (v/v) HCl in 70% (v/v) ethanol) were performed using a sensitive chemiluminescence enzyme-linked immunosorbent assay (ELISA; ALPCO, Salem, NH 03079). All experiments with human islets were approved by the Ethical Commission of the Human Research Act (Switzerland).

TABLE 5

| tested compounds | | |
|---|---|---|
| c1 | CA | Caffeic acid |
| c2 | CA3G | Caffeic-3'-O-glucuronide |
| c3 | CA3S | Caffeic-3'-O-sulfate |
| c4 | CA4G | Caffeic-4'-O-glucuronide |
| c5 | CA4S | Caffeic-4'-O-sulfate |
| c6 | DHCA | Dihydrocaffeic acid |
| c7 | DHCA3G | Dihydrocaffeic-3'-O-glucuronide |
| c8 | DHCA3S | Dihydrocaffeic-3'-O-sulfate |
| c9 | DHCA4G | Dihydrocaffeic-4'-O-glucuronide |
| c10 | DHCA4S | Dihydrocaffeic-4'-O-sulfate |
| c11 | DHFA | Dihydroferulic acid |
| c12 | DHFA4G | Dihydroferulic-4'-O-glucuronide |
| c13 | DHFA4S | Dihydroferulic-4'-O-sulfate |
| c14 | DHiFA | Dihydroisoferulic acid |
| c15 | DHiFA3G | Dihydroisoferulic-3'-O-glucuronide |
| c16 | DHiFA3S | Dihydroisoferulic-3'-O-sulfate |
| c17 | FA | Ferulic acid |
| c18 | FA4G | Ferulic-4'-O-glucuronide |
| c19 | FA4S | Ferulic-4'-O-sulfate |
| c20 | iFA | Isoferulic acid |
| c21 | iFA3G | Isoferulic-3'-O-glucuronide |
| c22 | iFA3S | Isoferulic-3'-O-sulfate |
| c23 | mDHCoA | 5-4-dihydro-m-coumaric acid |
| c24 | MeDHFA | Methyl Dihydroferulic acid |
| c25 | MeFA | Methyl Ferulic acid |

The invention claimed is:

1. A method for treating an increase in a plasma postprandial insulin concentration in a subject in need thereof, the method comprising administering to the subject as part of or at the end of a regular meal an effective dose of esterase treated decaffeinated green coffee extract with an amount of 40-200 mg/day, wherein the effective dose of esterase treated decaffeinated green coffee extract decreases the plasma postprandial insulin concentration in the subject.

2. The method according to claim 1, wherein the method induces glucose uptake in skeletal muscle cells of the subject.

3. The method according to claim 1, wherein the method improves pancreatic beta cell sensitivity to glucose in the subject.

4. The method according to claim 1, wherein the subject has a disorder selected from the group consisting of diabetes; impairment of glucose metabolism; hyperinsulinemia; and insulin resistance.

5. The method according to claim 1, wherein the subject is a diabetic or pre-diabetic patient.

6. The method according to claim 1, wherein the esterase treated decaffeinated green coffee extract is administered in a composition selected from the group consisting of a liquid beverage composition, a powder, and a snack bar.

7. The method according to claim 1, wherein the dose of the esterase treated decaffeinated green coffee extract comprises a total content of caffeic acid and ferulic acid between 10 and 60 mg.

8. The method according to claim 1, wherein the esterase treated decaffeinated green coffee extract comprises a ratio of caffeic acid:ferulic acid greater than 2:1.

9. The method according to claim 1, wherein the esterase treated decaffeinated green coffee extract comprises a ratio of caffeic acid:ferulic acid between 3:1 to 10:1.

10. The method according to claim 1, wherein the method further comprises administering a meal of at least 200 kcal to the subject.

11. The method according to claim 1, wherein the subject is a human.

12. The method according to claim 1, wherein the subject is at risk of developing type-2 diabetes, insulin resistance, or glucose intolerance.

13. The method according to claim 10, wherein the method decreases insulin concentration in plasma of the subject by at least 20% in comparison to consumption of the meal without administration of the esterase treated decaffeinated green coffee extract.

14. The method according to claim 10, wherein the esterase treated decaffeinated green coffee extract is administered as part of the meal.

15. The method according to claim 10, wherein the esterase treated decaffeinated green coffee extract is administered at the end of the meal.

16. The method according to claim 1, wherein the amount of esterase treated decaffeinated green coffee extract administered to the subject is 200 mg/day.

* * * * *